| United States Patent [19]<br>Moreno | [11] 4,260,602<br>[45] Apr. 7, 1981 |

[54] HAPTEN POLYSACCHARIDE CONJUGATE MEDICAMENTS AND METHOD OF USE

[75] Inventor: Carlos Moreno, Hayes, England

[73] Assignee: Burroughs Wellcome Co., Research Triangle Park, N.C.

[21] Appl. No.: 933,877

[22] Filed: Aug. 15, 1978

[30] Foreign Application Priority Data

Aug. 16, 1977 [GB] United Kingdom ............... 34279/77

[51] Int. Cl.³ ...................... A61K 31/73; C08B 37/02; A61K 31/715
[52] U.S. Cl. .................................... 424/180; 424/195; 424/228; 424/246; 424/251; 424/271; 536/1; 536/18; 536/112
[58] Field of Search ............... 424/180, 195, 228, 246, 424/251, 271; 536/1, 112, 18

[56] References Cited

U.S. PATENT DOCUMENTS

| 2,768,097 | 10/1956 | Novak et al. ........................ 536/112 |
| 2,880,105 | 3/1959 | Hiler ..................................... 536/112 |
| 3,063,905 | 11/1962 | Novak .................................. 536/112 |
| 3,063,906 | 11/1962 | Heckel et al. ........................ 536/112 |
| 3,130,126 | 4/1964 | Novak .................................. 536/112 |
| 3,931,398 | 1/1976 | Gaffar et al. ........................... 424/92 |

OTHER PUBLICATIONS

"Chem. Abst.", vol. 67, 1967, p. 106927(f).
"Chem. Abst." vol. 85, 1976, p. 92018(t).
"Chem. Abst." vol. 75, 1971, p. 149980(a).
Agrawal et al. "Chem. Abst.", vol. 70, 1969, p. 25,651w.
Grotsch et al. "Chem. Abst." vol. 73, 1970, p. 91,234a.

*Primary Examiner*—Johnnie R. Brown
*Attorney, Agent, or Firm*—Donald Brown

[57] ABSTRACT

The present invention provides conjugates between levan or dextran and a medicament, processes for preparing them, pharmaceutical compositions containing them and intermediates in their preparation. The conjugates create tolerance to the administration of the medicaments in mammals.

13 Claims, No Drawings

HAPTEN POLYSACCHARIDE CONJUGATE MEDICAMENTS AND METHOD OF USE

The present invention relates to conjugates which are formed between certain medicaments, in particular penicillins, and substituted levans said conjugates being useful in providing immunological tolerance in mammals to the administration of the medicaments. The invention also relates to processes for preparing and compositions containing such conjugates.

Many patients suffer from allergic reactions when prescribed particular drugs by their doctor, there being a wide range of drugs which can cause such reactions. In the case of particularly sensitive patients this may prevent certain drugs being prescribed thereby severely restricting the choice of drugs open to the doctor in this fight to combat disease.

The penicillins are a class of drugs which have become increasingly important in the last three decades for the treatment of bacterial infections. Unfortunately however, the penicillins can cause severe allergic reactions and anaphylaxis on administration to animals and humans. Over the past decade several attempts have been made to overcome these problems and to create immunological tolerance to the administration of penicillins and prevent anaphylaxis. Much of this work has been carried out on benzylpenicillin which is the drug most commonly causing allergic reactions. For example, Chiorazzi et. al (*Proc. Natl. Acad. Sci.* USA, 73, 2091, 1976) reported that the treatment of mice with the benzylpenicilloyl derivatised synthetic co-polymer of D-glutamic acid and D-lysine resulted in the suppresion of antibenzylpenicilloyl antibody responses and that the state of induced tolerance was highly specific and of long duration. Similarly Borel et al. (*Nature*, 261, 49, 1976) induced tolerance to benzylpenicillin by the administration of benzylpenicilloyl linked to several protein carriers and De Weck and Schneider (Int. Arch. Allergy, 42, 782, 1976) inhibited allergic reactions to benzylpenicillin in vivo by the administration of benzylpenicilloylformyllysine.

It has now been found that conjugates formed by linking certain medicaments or derivatives thereof to certain substituted haptens give good tolerance and are poorly immunogenic, that is to say they do not stimulate the production of appreciable amounts of antibodies, after the conjugates have been administered. Furthermore, it has been found that administration of these conjugates after the induction of an allergic reaction to the medicament from which the conjugate is derived effectively counteracts the observed allergic response.

By the term 'medicament' is meant a pharmacologically active substance useful in the field of medicine. The medicaments suitable for inclusion in the conjugates of this invention are those which cause an allergic reaction on administration to humans and animals and which contain at least one carboxy group or are modified to contain such a group. Commonly only one part of the medicament molecule or a metabolite of the medicament will cause the allergic reaction. For example, it is known that penicilloic acid and penicillamine are two metabolites of benzylpenicillin which contribute greatly to the allergic reaction observed when benzylpenicillin is administered. Thus metabolites of medicaments which cause an allergic reaction on administration, provided they contain at least that part of the molecule which is responsible for the allergic reaction and at least one carboxy group, are also suitable for inclusion in the conjugates of the present invention as derivatives of medicaments.

Haptens suitable for inclusion in the conjugates of the present invention are levans and dextrans.

Levans are natural polymers of 2,6- and 2,1-linked β-D-fructofuranose present in some bacteria and in grasses. Thus the repeating unit of levan has the formulae (I) and (II):

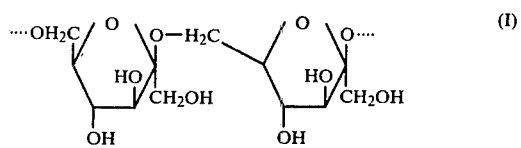

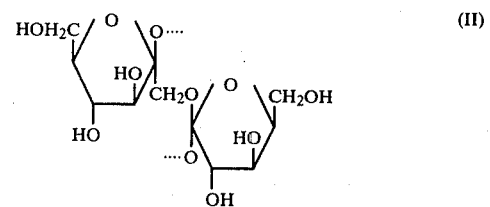

It can be seen that each furanose ring in levan has three free hydroxy groups to which substituents may be attached.

Dextran is a term applied to polysaccharides produced by bacteria growing on a sucrose substrate, containing a backbone of D-glucose units linked predominantly α-D (1-6).

According to the present invention there is provided a medicament-substituted hapten conjugate having a molecular weight of greater than 20,000, comprising a hapten in which a number of the hydroxy groups are substituted by one or more groups —$CH_2$—CO—NH—X—NHY, wherein X is a $C_{1-8}$ alkylene group optionally substituted by hydroxy groups of a $C_{2-8}$ alkyleneamino group, wherein Y is a medicament or derivative thereof as hereinbefore defined, the carboxy group in Y and the amino group in the substituent chain forming an amide linkage between the two. Particularly suitable medicaments for inclusion within the conjugates of this invention include penicillins, cephalosphorins, sulphonamides, benxylpyrimidenes, extracts of pollens and derivatives thereof, which contain carboxy groups. Suitable derivatives of penicillins include penicilloic acid and penicillamine. Suitable benzylpyrimidines include those of the formula (III):

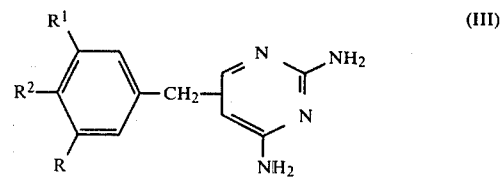

wherein one of R, $R^1$, $R^2$ is a —$CH_2$—CO— group and the others, which may be the same or different, are hydrogen, hydroxy, $C_{1-4}$ alkyl or $C_{1-4}$ alkoxy.

By the term X is a $C_{1-7}$ alkyleneamino group is meant that X may be a $C_{1-7}$ alkylene group substituted by one or more amino groups or that amino groups link together more than one alkylene group to form a $C_{1-7}$ alkyleneamino group. Conveniently X is a $C_{2-5}$ alkylene group and preferably a propylene group.

In a preferred aspect the present invention provides a penicilloyl-substituted hapten conjugate having a molecular weight of greater than 20,000 comprising a levan in which a plurality of the hydroxy groups are substituted by one or more groups —$CH_2$—CO—NH—X—NHY wherein X is as hereinbefore defined and Y is a group of the formula (IV):

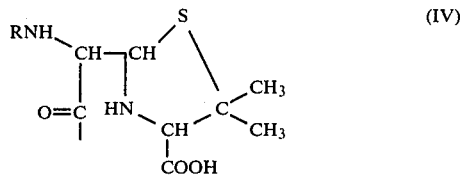

or a pharmaceutically acceptable salt or ester thereof wherein R is a hydrogen atom or an acyl side-chain conveniently linked to the amino group attached to the 6-position in naturally occurring or semi-synthetic penicillins.

Preferably R is a phenylacetyl group.

Pharmaceutically acceptable salts include sodium, potassium, calcium, magnesium, aluminium, ammonium and substituted ammonium salts. The sodium and potassium salts are particularly suitable.

Esters suitable for the purpose of this invention include those notionally derived from an alcohol ROH wherein R is an alkyl, alkenyl, alkynyl, aryl or aralkyl group which may be substituted if desired. Preferably the esters are in vivo hydrolysable esters such as the pivaloyloxymethyl or phthalimido esters.

In a further preferred aspect of the present invention provides a sulphonamide-substituted levan conjugate having a molecular weight of greater than 20,000 comprising a hapten in which a plurality of the hydroxy groups are substituted by one or more groups —$CH_2$—CO—NH—X—NHY wherein X is as hereinbefore defined and Y is a group

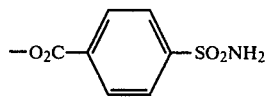

or a pharmaceutically acceptable salt thereof.

Preferably the hapten is a levan.

It has been found that although a degree of tolerance is induced when the conjugate has a molecular weight as low as 20,000 higher molecular weight conjugates are preferred, i.e. those with a molecular weight of at least in the order of $10^5$ and preferably at least in the order of $10^6$. It has also been found that the degree of induced tolerance is surprisingly increased when the number of Y groups, i.e. the medicament component, attached to the hydroxy groups of the hapten is increased. Whilst it has been found that tolerance may be induced with a hapten substituted by only 20 Y groups per 1,000 fructosyl residues the hapten is most suitably substituted by at least 60 and preferable by at least 90 Y groups per 1,000 fructosyl residues.

The conjugates of the present invention do not elicit passive cutaneous anaphylaxis, particularly when they are highly substituted, and are therefore preferable to the other known tolerogens. Furthermore the conjugates suppress the immune response to the hapten and are therefore free of potentially troublesome side effects due to the hapten.

The present invention also provides a process for preparing medicament-substituted hapten conjugates which process comprises the reaction of a medicament, or derivative thereof, as hereinbefore defined with a hapten in which a number of the hydroxy groups are substituted by a group of the formula (V):

—$CH_2$—CO—NH—X—$NH_2$  (V)

wherein X is as hereinbefore defined.

In the case of penicillins the reaction will normally be carried out in an aqueous solvent, conveniently water, and at alkaline pH, for example at a pH of greater than 9. This may conveniently be achieved by buffering the solution with a conventional alkaline buffer such as carbonate buffer. Carrying out the reaction at alkaline pH converts the penicillin to a penicilloly moiety which reacts with the substituted levan to give a penicilloyl-substituted hapten conjugate.

The reaction will be carried out at a non-extreme temperature, for example between 0° and 100° C., and may conveniently be carried out at room temperature.

In the case of other medicaments or derivatives thereof hereinbefore defined the reaction may conveniently be carried out in the presence of a conventional condensation promoting agent such as a carbodiimide. The reaction is normally carried out at acid pH, suitably between 4.5 and 6.5, and at a non-extreme temperature, i.e. between −10° C. and 100° C., and conveniently at room temperature, in a suitable solvent, for example water or a mixture of water with a water miscible organic solvent.

Alternatively the carboxylic acid group of the medicament or derivative thereof may be converted into an N-acylating derivative by methods well known to those skilled in the art. Suitable N-acylating derivatives include acid halides and anhydrides. The N-acylating derivative is then reacted with the substituted levan under conditions well known to those skilled in preparing amides.

Haptens in which a number of the hydroxy groups are substituted by a group of the formula (V), as hereinbefore defined, are usful intermediates and as such form part of the present invention. These intermediates may be prepared by the reaction of a hapten in which a number of the hydroxy groups are substituted by a group of the formula: —$CH_2CO_2H$, or a reactive N-acylating derivative thereof, with a compound $H_2NXNH_2$, wherein X is as hereinbefore defined.

Suitable N-acylating derivatives of the carboxylic acid group include acid halides and anhydrides. The reaction may conveniently be carried out by the reaction of the free carboxylic acid group with a compound $H_2NXNH_2$ in the presence of a condensation promoting reagent such as a carbodiimide. This reaction is normally carried out at acid pH, suitably between 4.5 and 6.5, and at a non-extreme temperature, i.e. between −10° and 100° C. and conveniently at room temperature, in a suitable solvent, for example water or a mixture of water with a water miscible polar organic solvent.

The hydroxy groups of the hapten may readily be substituted by the group: —$CH_2CO_2H$, by the reaction of the hapten with a suitable reactive derivative of acetic acid, for example a monohaloacetic acid such as monochloroacetic acid. This reaction is carried out in an aqueous solvent system at alkaline pH at a non-extreme temperature. The reaction is suitably carried out in aqueous sodium hydroxide at a pH of greater than 12 at room temperature.

In a further aspect this invention provides a pharmaceutical composition for the purpose of medical or veterinary treatment which comprises a medicament substituted hapten conjugate hereinbefore defined as a substance in a form or shape, e.g. together with a pharmaceutically acceptable carrier or in combination with a carrier, for instance in a sealed or sterile state, or in a dosage form.

The compositions of the invention include those in a form adapted for oral, topical or parenteral use and may be used for the treatment of immune hypersensitivity in mammals including humans.

Suitable forms of the compositions of this invention include tablets, capsules, creams, syrups, suspensions, solutions and sterile forms suitable for injection or infusion. Such compositions may contain conventional pharmaceutically acceptable materials such as diluents, binders, colours, flavours, preservatives, disintegrants and the like in accordance with conventional pharmaceutical practice.

Injectable compositions containing the medicament substituted hapten conjugates, especially injectable compositions suitable for intravenous admininstration, are particularly preferred compositions of this invention. Such compositions will be made up in a sterile form in an aqueous solvent vehicle, such as aqueous polyethylene glycol, or saline. Saline, which may be buffered to physiological pH as required, is a particularly suitable solvent vehicle.

The compositions of the present invention are prepared by conventional formulation techniques well known to those skilled in the art, for example the injectable compositions are prepared by adding the medicament-substituted conjugates to the aqueous solvent vehicle and sterilising the resultant solution.

In a yet further aspect the present invention provides a method of treatment of immune hypersensitivity to a medicament in mammals, including humans, which comprises the administration of an effective dose of the appropriate medicament substituted hapten conjugate hereinbefore defined.

The invention also provides a method of treatment of bacterial infections in mammals, including humans, which comprises the administration of an effective dose of a medicament substituted hapten conjugate hereinbefore defined, wherein the medicament in the conjugate is an antibacterially active medicament.

Suitably between 0.01 mg/kg and 100 mg/kg and conveniently 1 mg/kg of the medicament substituted hapten conjugate will be administered daily.

The conjugates of the present invention may be administered to induce immunological tolerance to a medicament so that the patient may then receive a course of treatment with that particular medicament or they be administered when a patient is suffering from an allergic reaction to a medicament to induce tolerance to that medicament. In the latter case the degree of substitution of the hapten needs to be higher than it is in the former. The dosage level of the conjugates of the invention will also normally be higher in this case.

Immunogenic Properties of the Conjugates of the Invention

The capacity of pen-HSA (ovalbumin and human serum albumin coupled to the potassium salt of benzylpenicillin), Pen-DAP(1)-CM-LE (a penicilloyl-diaminopropylcarboxymethyl levan conjugate containing 22 pencillin groups/1000 fructosyl residues), Pen-DAP(2)-CM-LE (a penicilloyl-diaminopropylcarboxymethyl levan conjugate containing 95 penicillin groups/1000 fructosyl residues), and Pen-DAP-CM-LE (XM50) (a penicilloyl-diaminopropylcarboxymethyl levan conjugate of low molecular weight (M.W. = 3400) to react with goat anti-Pen serum (containing 6.5 mg precipitating antibody per ml) was measured by direct precipitation and by inhibition of precipitation between the same anti-Pen goat serum and Pen-HSA. The results are shown in Table 1.

TABLE 1

| Immunoprecipitation of antibody expressed as % of antibody precipitated by Pen-HSA | |
|---|---|
| Pen - DAP(1)-CM-LE | 53% |
| Pen - DAP(2)-CM-LE | 78% |
| Pem - DAP-CM-LE(XM50) | ~0% |

The relevance of these results to allergy in mice was investigated by inhibition of PCA (passive cutaneous anaphylaxis) reactions. This reaction was measured incubating a constant dilution of antiserum calculated to give 10 mm PCA spot) with different amounts of inhibitor for 1 hour at room temperature. Fifty (50) $\mu$l samples from each mixture were injected into the skin of Wistor rats that were challenged 24–48 hours later with 2.5 mg Pen-HSA and 5 mg of Evans blue (i.v.). The capacity of the compounds to inhibit PCA was indicated by a decrease in the size of the blue spot in the skin. All three compounds listed in table 1 inhibited specific anti-Pen antibodies. Using amounts of 80, 15 and $2 \times 10^4$ ng/site respectively (in the order listed in Table 1) 50% inhibition was achieved.

The capacity of the same compounds to elicit a direct PCA was measured. Several dilutions (50 $\mu$l) of anti-Pen serum were injected in the skin of rats and one day later thay were injected in the same spot with 1 or 50 $\mu$g or antigen right after i.v. injection of Evans blue. The results are shown in Table 2.

TABLE 2

| Direct PCA reaction with mouse anti-Pen and penicilloyl substituted levans | | | | |
|---|---|---|---|---|
| | Antiserum Dilution | | | No |
| Antigen ($\mu$g/site) | 1/10 | 1/20 | 1/40 | antiserum |
| Pen-HSA (50) | 13 | 9 | 8 | 5 |
| (1) | 15 | 10 | 8 | 5 |
| Pen-DAP(1)-CM-LE (50) | 11 | 7 | 6 | 6 |
| (1) | 11 | 9 | 6 | 5 |
| Pen-DAP(2)-CM-LE (50) | 5 | 5 | 5 | 5 |
| (1) | 5 | 5 | 5 | 5 |
| Pen-DAP-CM-LE(XM50) (50) | 5 | 5 | 5 | 5 |
| (1) | 5 | 5 | 5 | 4 |

Tolerance Induction Properties of the Conjugates of the Invention

The tolerance capacity of Pen-DAP-CM-levans was examined first by injecting them into mice 2 and 3 weeks before the immunisation scheme. CBAT6T6 and DBA/2 inbred strains of mice, bred by the Immunobiology Department of the Wellcome Foundation Limited, were immunised as shown in Diagram 1. The immunogen (penicilloyl oralalbumin-Pen-OV) was mixed with aluminium sulphate containing 0.02% phenol red as indicated and precipitated with sodium hydroxide just prior to injection. Immediately after precipitation,

*B. pertussis* vaccine was added and the volume made up with saline to give 0.2 ml/mouse. Polysaccharides were injected i.v. (0.2 ml/mouse) diluted in phosphate-buffered saline. DBA/2 and CBAT6T6 mice respond to high and low doses of immugen respectively.

To stimulate the production of IgE antibodies 300 larvae of *Nippostrongylus brasiliensis* were injected subcutaenously in the back of the neck (0.2 ml/mouse).

The modified Jerre PFC (plaque forming cell) assay (Immunology 23, 843, 1972) was used to determine direct (IgM) splenic PFC specific for Penicilloyl and levan determinants. Estimation of IgE titres was carried out by titrating each serum independently. The animals were bled only once and serial dilutions of the sera (50 μl samples) injected i.v. in the skin of Wistar rats for PCA.

Heterologous cell transfer (HCT) was measured by the method of KInd & Sobrinho (J. Immunol. 111, 638, 1973). Duplicate 50 and 100 μl samples of washed spleen suspensions in 199 medium (Burroughs Wellcome) were injected into the skin of Ag-B5 HO rats. Twenty-four hours later the animals were challenged in the same way as for PCA reactions and the diameter of the blue spots measured. The number of spleen cells secreting IgE antibodies specific for Pen or OV was assumed to be proportional to the area of the blue spots.

The results in Table 3 indicate that 1 doses of Pen-(1)CM-LE and Pen-DAP(2)CM-LE suppressed severely the IgE anti-Pen titre (PCA) measured 2 and 3 weeks after boost with Pen-OV. IgM and IgG PEC/-spleen were very low in the immune controls. Both polysaccharide derivatives slightly increased the former and decreased the latter.

To demonstrate that the suppression reflected a diminished number of cells synthesising IgE antibody, rather than peripheral neutralization, the immune response was measured in the spleen of the same animals (Table 3, HCT). The size of the skin reaction in this heterologous transfer is a reflection of the number of cells secreting IgE antibodies, and it is clear from the data presented that tolerance induction resulted in a substantial decrease of spleen cells forming anti-Pen antibodies of the IgE class. A similar experiment was performed using CBA mice, but this time the tolerogen was given after priming, to avoid the problems resulting from the fact that CBA mice had to be immunized several times with low doses of antigen (see Diagram 1) to achieve immunity. At the time of tolerogen injection, anti-Pen PCA titres were 1/10. Results of such experiments are presented in Table 4. It is clear that suppression of the immune response also took place in this strain even when tolerogen was given after priming. As with DBA/2 mice the low PCA titre corresponded with smaller numbers of anti-Pen IgE cells in the spleen.

Whether the induction of tolerance could be achieved in mice already showing a high reaginic response was tested according to the following experimental scheme: DBA/2 mice primed, infected and boosted as described in Diagram 1 were tested for anti-Pen IgE. On day 33 they were all allergic ($\bar{X}=1/42$). On day 47, PCA titres were low (3 positives out of 5, PCA titre 1/23). Subsequently (day 55) mice were divided into 3 groups, the first treated with Pen-DAP(1)-CM-LE, the second with Pen-DAP(2)-CM-LE and the third left as control. Two weeks later they were all boosted in the same way. PCA, HCT, IgM and IgG PFC were measured 14 days after the boost (see Table 5). The results clearly indicate that the highly substituted Pen-DAP(2)-CM-LE provoked a very marked tolerance but the more weakly substituted Pen-DAP(1)-CM-LE only gave a partial, non-significant, suppression. As in the previous experiments, very low spleen IgM and IgG PFC numbers were found. The lack of responsiveness persisted after HCT of the spleen cells.

Preparation of Penicilloyl-diaminopropyl-carboxymethyl-levan (1) Preparation of carboxymethyl-levan Purified levan (3 g) from *Corynebacterium levaniformis* was dissolved in water (150 ml) and mixed with 10 N sodium hydroxide (12 ml) and monochloroacetic acid (3 g), stirred for 1 hour at room temperature and at 60° C. for 3 hours, neutralised (pH 7) with 5 N hydrochloric acid and dialysed at 4° C. for 3 days (checking the conductivity of the water). The material was frozen, dried and analysed for sugar and carboxylic groups (156-COONa/1000 fructosyl residues). The yield was 3.1 g.

(2) Preparation of diaminopropyl-carboxymethyl levan

A 2% of carboxymethyl-levan (50 ml) was mixed with 1-ethyl-3-(3-dimethylaminopropyl)carbodiimide (0.4 g) in 20% molar excess to the carboxylic groups. The pH was adjusted to 5–6 and at 50 times molar excess of preneutralised diaminopropane (6.4 g) was added at once. The mixture was stirred at room temperature for 24 hours and for the first 3 hours the pH was maintained between 5 and 6. This material was then dialysed at 4° C. against 0.01 N sodium hydroxide first and water later, analysed for free amino groups by ninhydrin and the purity checked by gel filtration (Sephadex G-75). The yield was 1.8 g 11% of the carboxy groups had coupled with diaminopropane.

Repetition of the example using different relative amounts of the carbodiimide and diaminopropane alters the degree of substitution of the diamino-carboxymethyl-levan.

(3) Preparation of penicilloyl-diaminopropyl-carboxymethyl-levan

Diamino-carboxymethyl-levan (1 g) obtained from (2) was dissolved in a 10% sodium carbonate solution (50 ml) and potassium benzylpenicillin (4 g) added and dissolved. The solution was kept for two days at room temperature and dialysed at 4° C., frozen and dried (1 g). A full substitution of the amino groups was obtained.

Preparation of Penicilloyl-triethylenetetramino-carboxymethyl-levan

The above conjugate was prepared by exactly the same method as penicilloyl-diaminopropyl-carboxymethyl-levan, triethylenetetramino being substituted for diaminopropane.

Preparation of Penicilloyl-triethylenetetramino-carboxymethyl-dextran

The above conjugate was prepared in a similar manner to the levan analogue by substituting dextran (molecular weight about $2 \times 10^6$) for levan.

Penicilloyl-triethylenetetramino-carboxymethyl-levan and penicilloyl-triethylenetetramino-carboxymethyl dextran were tested in mice infected with *Nippostrongylus brasiliensis* as described previously for Pen-DAP-CM-LE and found to induce tolerance.

Preparation of Penicilloyl-diaminopropyl-carboxymethyl-dextran

This was prepared as described above for the levan equivalent but substituting dextran (mol. wt. about $2 \times 10^6$) for levan.

Preparation of 4-Sulphonamidobenzoyl-diaminopropyl-carboxymethyl-levan

To a solution of diaminopropyl-carboxymethyl-levan (1 g, prepared as described above) and 4-sulphonamidobenzoic acid (1 g) was added 1 ethyl-3 (3-dimethylaminopropyl)carbodiimide hydrochloride (10 g) and the pH then adjusted to 8–9 with 1 N NaOH. The solution was kept at ambient temperature for 2 days, the pH being maintained at the aforementioned value. The reaction mixture was then dialysed against water for 4 days at 4° C. and freeze-dried to give product, (SABA-DAP-CM-LE).

Mice were injected with 4-sulphonamidobenzoic acid coupled to chicken gamma globulin (SABA-CGG). The allergic response to (SABA-CGG) in the mice showed cross-reaction with sulphadiazine and sulphaguanidine as measured by inhibition of PCA reactions. A number of the mice were then tolerized with SABA-DAP-CM-LE and sulphamethoxazole, sulphaguanidine and SABA-ovalbumin injected into separate groups of tolerized and untolerized mice. The tolerized mice survived while the untolerized mice died. The EIgE anti-body titres of the tolerized mice were very low compared to those of the untolerized mice.

Different degrees of substitution can be obtained by changing the proportion of components and the degree of substitution of the diaminopropyl-carboxymethyl-levan used.

Diagram 1

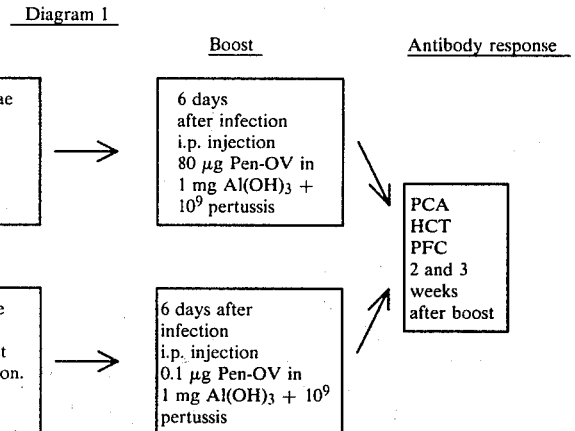

TABLE 3

The effect of high mol. weight Pen-DAP-CM-levans administered prior to induction of allergy to penicilloyl determinants in DBA/2 mice*

| | | Anti-Pen Immune Response+ | | | | | | | |
|---|---|---|---|---|---|---|---|---|---|
| | | 2 weeks after boost | | | | 3 weeks after boost | | | |
| | Tolerogen (day 0) | PCA | HCT$^f$ | IgM§ | IgG§ | PCA | HCT | IgM | IgG |
| Exp. 1 | 1 mg Pen-DAP(1)-CM-NLE (i.v.) | <1/5 | n.d.‡ | 990 (1.34) | 307 (1.63) | <1/5 | n.d. | 299 (1.49) | 179 (1.51) |
| | NIL | 1/82 (1.48) | n.d. | 187 (1.53) | 680 (1.36) | 1/35 (1.34) | n.d. | 112 (1.12) | 257 (1.57) |
| Exp. 2 | 1 mg Pen-DAP(2)-CM-NLE (i.v.) | 1/7 (1.70) | <1 | 375 (1.30) | 105 (1.05) | <1/5 | <1 | <100 | <100 |
| | NIL | 1/84 (1.17) | 20.9 (2.0) | 255 (1.38) | 336 (1.68) | 1/79 (1.42) | 6.0 (2.5) | <100 | 200 |

*Immunization according to Diagram 1, for Exp. 1 priming, infection and boosting on days 15, 31 and 38 respectively. For Exp. 2, priming, infection and boosting took place on days 23, 44 and 50, respectively.
† Results as geometric means of 5 animals; standard error in parentheses.
$^f$ Blue area in mm.
§ Direct (IgM) and indirect (IgG) PFC/spleen.
‡ Not done.

TABLE 4

Tolerogenicity of high mol. weight Pen-DAP-CM-Levans on IgE response of CBA mice*

| | Anti-Pen immune response† | | |
|---|---|---|---|
| | 2 weeks after boost | 3 eeks after boost | |
| Tolerogen | PCA† | PCA | HCT$^f$ (mm²) |
| Pen-DAP(1)-CM-NLE | <1/10 | <1/5 | <1 |
| Pen-DAP(2)-CM-NLE | <1/10 | <1/5 | <1 |
| Nil | 1/63 (1.73) | 1/23 (2.2) | 12.6 (1.59) |

Immunization according to Diagram 1.
*Priming: days 0, 28 and 59.
Tolerogen: day 78
Infection (N.b): day 79
Boost: day 85
† Geometric average of 5 mice. Standard error in parenthesis.
$^f$ Area of the blue spot (mm²).

TABLE 5

Induction of tolerance in DBA/2 mice already allergic to Penicilloyl groups*

| | | Immune response (day 83) † | | | |
|---|---|---|---|---|---|
| | No. of animals | | | PFC/spleen | |
| Tolerogen (day 55) | per group | PCA | HCT (mm²) | IgM | IgG |
| Pen-DAP(1)CM-NLE | 7 | 1/59 (1.31) | 14.7 (1.15) | 880 (1.33) | 1870 (1.28) |
| Pen-DAP(2)CM-NLE | 6 | 1/18 (1.73) | 5.9 (1.37) | 940 (1.41) | 2400 (1.26) |

TABLE 5-continued

| | | Immune response (day 83)† | | | |
|---|---|---|---|---|---|
| | No. of animals | | | PFC/spleen | |
| Tolerogen (day 55) | per group | PCA | HCT (mm$^2$) | IgM | IgG |
| NIL | 5 | 1/149 (1.68) | 24.9 (1.19) | 630 (1.88) | 3630 (1.34) |

Immunization according to Diagram 1.
*Priming: day 0
Infection (N.b.): day 14
Boost: day 20
Test for PCA: days 33 and 47
Tolerogen: day 55
Boost: day 69
Immune response: day 85.
†Results expressed as geometric means (standard errors in parenthesis).

What is claimed is:

1. A medicament-substituted hapten conjugate having a molecular weight of greater than 20,000, comprising a hapten selected from the group consisting of levane and dextrans in which a plurality of the hydroxy groups are substituted by one or more groups —CH$_2$—CO—NH—X—NHY, wherein X is a C$_{1-8}$ alkylene group optionally substituted by hydroxy groups or a C$_{2-7}$ alkyleneamino group, and Y is a medicament which causes an allergic reaction on administration to humans and animals and which contains a carboxy group or has been modified to contain such a group or a metabolite of such a medicament which contains a part of the molecule which is responsible for the allergic reaction and a carboxy group, the carboxy group in Y and the amino group in the substituent chain forming an amide linkage between the two.

2. A medicament-substituted hapten conjugate according to claim 1 wherein Y is a group of the formula (IV):

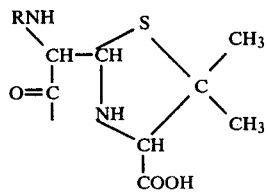

or a pharmaceutically acceptable salt or ester thereof, wherein R is a hydrogen atom or an acyl side-chain conveniently linked to the amino group attached to the 6-position in naturally occurring or semi-synthetic penicillins.

3. A medicament-substituted hapten conjugate according to claim 2 wherein R is a phenylacetyl group.

4. A medicament-substituted hapten conjugate according to claim 1 wherein Y is a group:

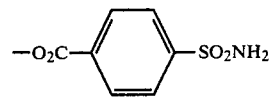

or a pharmaceutically acceptable salt thereof.

5. A medicament-substituted hapten conjugate according to any one of claims 1-4 wherein X is a propylene group.

6. A medicament-substituted hapten conjugate according to claim 5 wherein the molecular weight is at least in the order of 10$^6$.

7. A medicament-substituted hapten conjugate according to claim 6 wherein the hapten is a levan.

8. A medicament-substituted levan conjugate according to claim 7 wherein the levan is substituted by at least 90 Y groups per 1,000 fructosyl rsidues.

9. A pharmaceutical composition which comprises a medicament-substituted hapten conjugate, according to claim 1, together with a pharmaceutically acceptable carrier.

10. A pharmaceutical composition according to claim 9 in the form of an injectable composition suitable for intravenous administration.

11. A hapten, in which a number of the hydroxy groups are substituted by a group of the formula (V):

$$—CH_2—CO—NH—X—NH_2 \quad (V)$$

X is a C$_{1-8}$ alkylene group optionally substituted by hydroxy, or a C$_{2-8}$ alkyleneamino group.

12. A method for the treatment of immune hypersensitivity to a medicament in a mammal which comprises the administration of an effective dose of the appropriate medicament substituted hapten conjugate as defined in claim 1.

13. The medicant-substituted hapten conjugate of claim 1 in which the medicant is a penicillin, cephalosphorin, sulphonamide, benzylpyrimidine, extract of pollen and a derivation thereof which contains carboxy groups.

* * * * *